United States Patent [19]

Mathieu

[11] Patent Number: 4,745,950

[45] Date of Patent: May 24, 1988

[54] CONNECTOR FOR PERITONEAL DIALYSIS

[75] Inventor: Bernd Mathieu, Spiessen-Elfersberg, Fed. Rep. of Germany

[73] Assignee: Fresenius AG, Bad Homburg, Fed. Rep. of Germany

[21] Appl. No.: 850,854

[22] Filed: Apr. 11, 1986

[30] Foreign Application Priority Data

Apr. 12, 1985 [DE] Fed. Rep. of Germany ....... 3513205

[51] Int. Cl.$^4$ .......................... A61M 5/14; A61M 1/28
[52] U.S. Cl. .................................... 137/798; 210/234; 210/251; 251/149.1; 251/149.6; 604/29; 604/33; 604/905
[58] Field of Search ...................... 604/29, 30, 33, 34, 604/247, 249, 905; 210/234, 321.2, 927, 321.3, 321.72-321.81, 251, 541; 137/240, 798, 846, 849; 251/149.1, 149.2, 149.6

[56] References Cited

U.S. PATENT DOCUMENTS

| 4,019,512 | 4/1977 | Tenczar | 604/905 X |
| 4,338,933 | 7/1982 | Bayard et al. | 604/905 X |
| 4,346,703 | 8/1982 | Dennebey et al. | 604/905 X |

FOREIGN PATENT DOCUMENTS

| 29526 | 6/1981 | European Pat. Off. |
| 50255 | 4/1982 | European Pat. Off. |
| 80379 | 6/1983 | European Pat. Off. |
| 116986 | 8/1984 | European Pat. Off. |
| 135140 | 3/1985 | European Pat. Off. |

Primary Examiner—Richard V. Fisher
Assistant Examiner—W. Gary Jones
Attorney, Agent, or Firm—Poms, Smith, Lande & Rose

[57] ABSTRACT

A connector (2) for peritoneal dialysis comprises a female connector piece (4) and a male connector piece (6). The male connector piece comprises a central tube section (22) whose diameter tapers at a step (26). Furthermore, the female connector piece (4) comprises a valve means (52) which consists of an annular seal (54) and a valve plate (58) which is pressed by means of a pressure spring (60) against the sealing ring (54). On connection of the female connector piece (4) with the male connector piece (6) at least one pin (46) on the male connector piece engages in a guide groove (48) which is formed in a sleeve (10) in which the female connector piece (4) is provided. The guide groove (48) comprises a staircase or step-like form so that the female connector piece (4) can assume relatively to the male connector piece (6) three defined connection states, said three connection states effecting that the tube section (22) in cooperation with the valve means (52) releases or blocks fluid passages between a first connection (18), a second connection (32) and a third connection (36). The third connection (36) serves for connecting an empty bag for the used dialysis solution and is arranged together with the first connection (18) for the supply of fresh dialysis solution on the male connector piece (6).

13 Claims, 4 Drawing Sheets

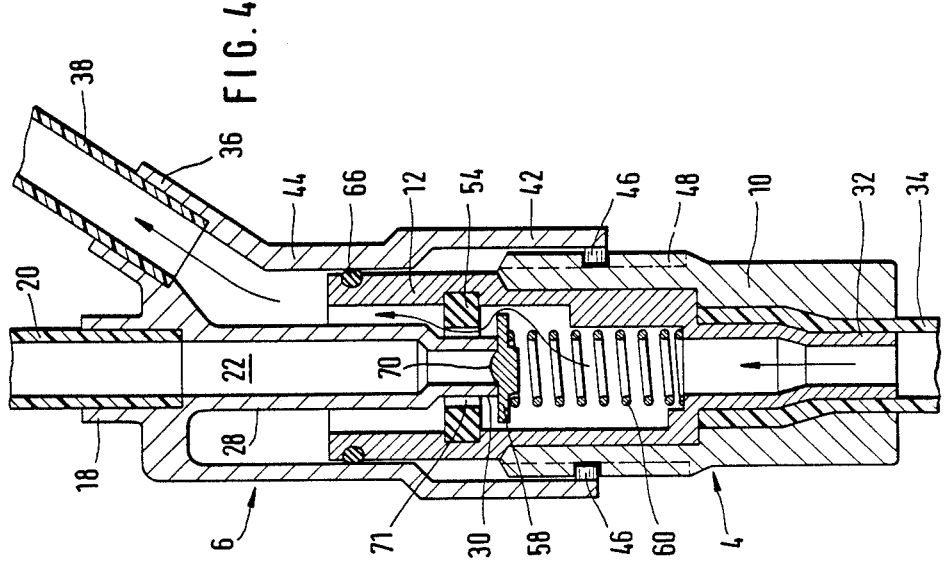
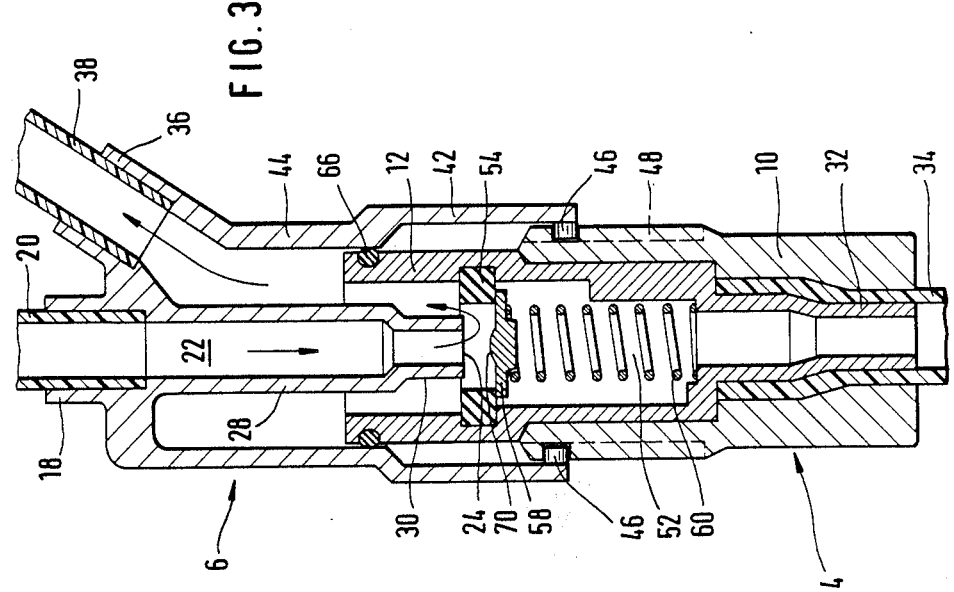

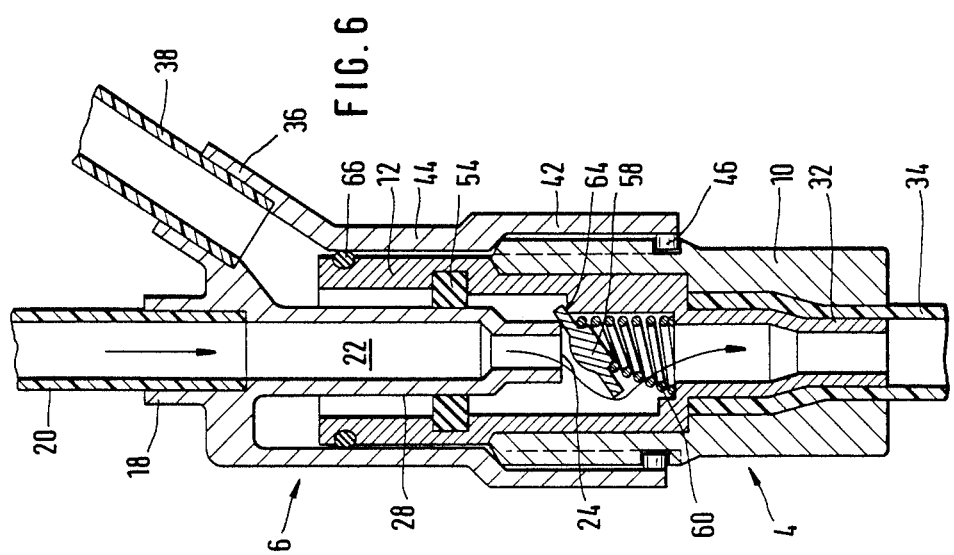
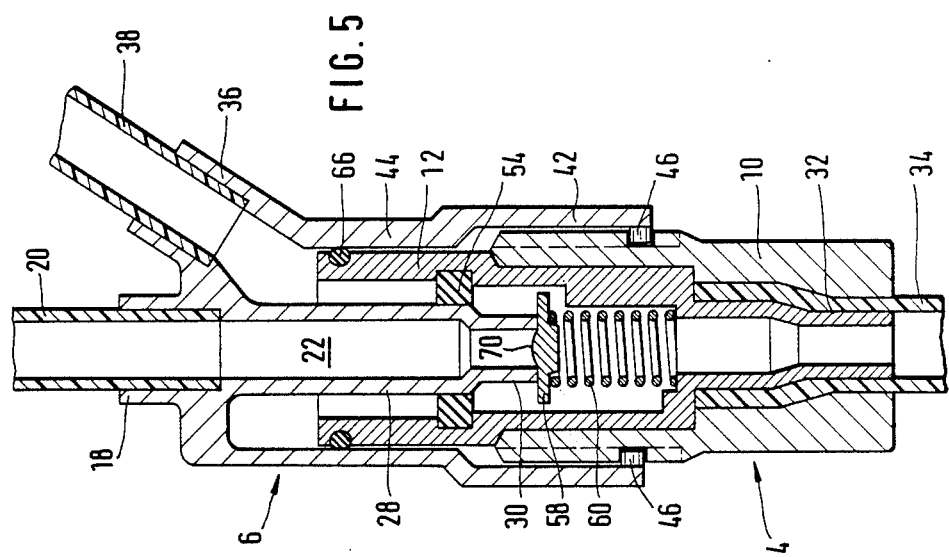

CONNECTOR FOR PERITONEAL DIALYSIS

The invention relates to a connector for a CAPD tube connection to a male connector piece having a central tube section which is engaged and surrounded by a protective sleeve, and a fenale connector piece which comprises a valve means which in the uncoupled state represents a fluid barrier, the introduction portion being introducible in liquid-tight manner into a receiving region of the protection sleeve with a seal between the protective sleeve and the female connector piece, a first connection on a male connector piece for a full bag with dialysis solution, the first connection being in fluid connection with the central tube section, a second connection on the female connector piece to which a peripheral catheter is connectable, and a connecting means for securing a connection position between the female and the male connector piece.

Such a connector is described for example in German utility model No. 7,836,790 or EP-OS No. 116,986. Such a catheter is used in continual ambulant peritoneal dialysis (CAPD) in which a catheter remains permanently in the peritoneal cavity of a patient. Such a catheter projects through the abdominal wall of a patient and is connected to one part of the connector, the other part of the connector being connected via a flexible tube to a bag containing dialysis solution. In the connected state the dialysis solution can be supplied to the patient for removing metabolism products and also removed from the patient again.

Problematical in such dialysis treatment is the replacement of a bag containing used dialysis solution by a bag containing fresh dialysis solution because the connector must be opened and this must take place under absolutely sterile conditions. The patient must open the connector with extreme care, the used bag being dispensed with and replaced by a fresh bag with a corresponding new sterile connector piece.

The connector of the type mentioned at the beginning already comprises a protective sleeve on the male connector piece and it is not possible for the corresponding connecting faces of the connector to come into contact with the fingers. Furthermore, in the connected state between the connector pieces a space to be filled with disinfectant is provided which is intended to eliminate any contaminations which may nevertheless arise. However, this known connector can only be used by specially trained patients who carry out these measures correspondingly carefully and exactly. With elderly or weak patients the problems in handling this connector are obvious so that further solutions of these problems were sought.

Thus, for example, EP-OS No. 29 526 proposes a bag system for peritoneal dialysis in which from the peritoneal catheter or from the connecting tube in Y manner a further tube branches which is connected to a further bag. All flexible tube portions can be closed by clips or clamps so that specific fluid passages may be opened or closed. Thus, dialysis solution can be conveyed from the full bag through the connector into the peritoneal cavity, from the full bag through the connector into the empty bag and from the peritoneal cavity into the empty bag.

This known system with Y-shaped branching has however the disadvantage that simple plug members are used for a connector which are not secured against contamination; in addition, the Y-shaped branching is one of the flexible tube sections so that solution residues which may be contaminated or a risk to the patient due to toxicity (disinfectant) can reach the peritoneal cavity of the patient. There is also a danger that particles which might be generated when the male connector piece is opened can also reach the body of the patient.

As a result, for a thorough flushing or rinsing of the male connector piece or the entire connector firstly careful handling of the roller clamps is necessary to enable the flushing operation to be carried out properly without any danger to the patient and secondly a considerable amount of water is wasted for pure flushing purposes.

Further connectors for medical purposes, although not for use in CAPD, are known from EP-OS No. 135 140 and No. 80 379. These connectors are effectively concerned only with a reliable closure of a connector piece in the unconnected state but not with complete sterility on connection.

The problem underlying the present invention is therefore to provide a connector for a dual-bag system according to the preamble of claim 1 which obviates the aforementioned disadvantages, i.e. in which troublesome roller clamps complicated to handle are dispensed with and a rapid and reliable flushing of the connector with a minimum of dialysis solution is possible.

This problem is solved in that on the male connector piece in the region of the first connection on the protective sleeve a third connection is disposed for an empty bag for used dialysis solution and that the valve means in dependence upon the connection possible of the female connector piece relatively to the male connector piece and in cooperation with the central tube section of the male connector piece free or interrupt fluid passages between the first, second and third connections.

In accordance with claim 1 the fluid passages between the full bag, peritoneum and empty bag are freed and interrupted in accordance with the particular requirements in dependence upon the connection state of the male connector piece relatively to the female connector piece, the connection for the empty bag being disposed on the female connector in the region of the connection for the full bag so that on the one hand roller clamps can be dispensed with, because the fluid passages are freed or interrupted solely by corresponding manipulations of the connector, and on the other hand by dispensing with a Y piece between the female connector and the peritoneal catheter only the connector itself and not the associated flexible tubing need be flushed so that the flushing operation itself can be carried out in relatively short time with small expenditure of dialysis solution.

DE-OS No. 2,853,635 and U.S. Pat. No. 4,346,703 disclose connectors for CAPD of the type mentioned at the beginning which each comprise a male and female connector piece which are each connected to flexible tubing. Since these connectors in the coupled state free the flow connection between the peritoneal cavity and the bag, the tubing must always appropriately be shut off by a clamp to prevent unintentional exit or entry of the dialysis solution from the bag or into the bag. Furthermore, the connector itself cannot be completely cleaned from residual disinfectant and consequently there is a danger that residual disinfectant can reach the peritoneal cavity of the patient during the filling with fresh dialysis solution.

The subsidiary claims contain advantageous further developments of the invention.

Further details, features and advantages of the present invention will be apparent from the following description of an example of embodiment with the aid of the drawings, wherein:

FIG. 3 shows in sectional view the position of the male connector piece with respect to the female connector piece in a first connection state;

FIG. 4 shows the position of the male connector piece with respect to the female connector piece in a second connection state;

FIG. 5 shows the position of the male connector piece to the female connector piece in a third connection state;

FIG. 6 shows the position of the male connector piece to the female connector piece in a fourth connection state.

Figure 2:
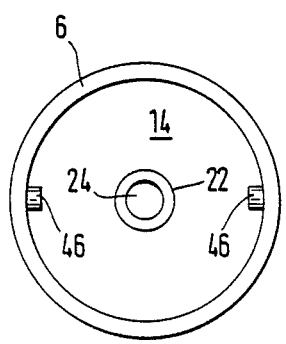
FIG. 2 is a plan view from below of the male connector piece.
Figure 1:
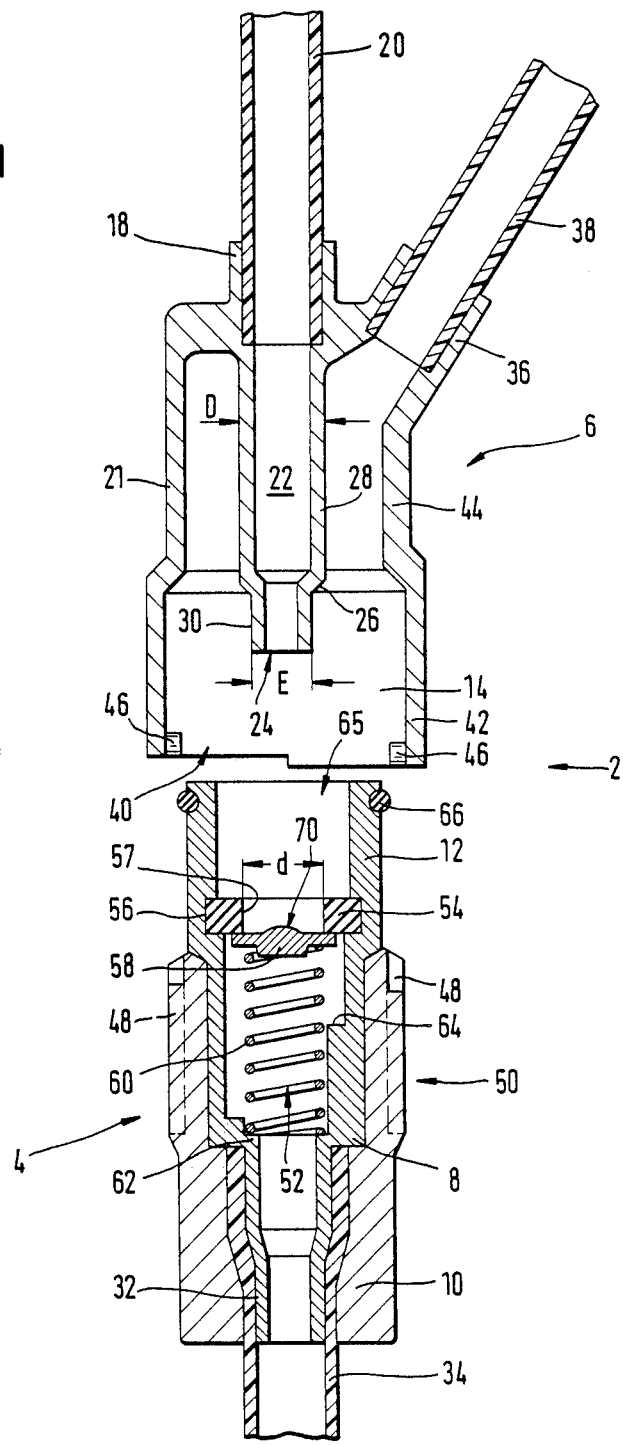
FIG. 1 is a sectional view of a connector according to the invention comprising a male connector piece and a female connector piece, the two connector pieces being shown in the unconnected state.

In accordance with FIG. 1 a connector 2 comprises a female connector piece 4 and a male connector piece 6. The female connector piece 4 comprises a connector unit 8 which is mounted in a first sleeve 10 behind an introduction portion 12.

Male connector piece 6 comprises a receiving region 14 for receiving the female connector piece 4. Furthermore, the male connector piece 6 comprises at its end opposite the receiving region 14 a first connection 18 for a flexible tube 20, the tube 20 establishing the connection line between a full bag with fresh dialysis solution not illustrated in the drawings and the male connector piece 6. The securing of the tube 20 to the first connection 18 may for example be by adhering or the like. As apparent from the drawings, the connection 18 extends through the sleeve 21 and merges in the direction towards the receiving region 14 into a central tube section 22 which is arranged coaxially with the sleeve 21 in the male connector piece 6 and comprises in its front portion 30 a mouth opening 24.

As further apparent from the drawings, the external diameter of the tube section 22 is not constant considered over its entire length; on the contrary, the tube section 22 comprises a main portion 28 which at a step 26 merges into a front portion 30 whose external diameter is less than that of the main portion 28. Both portions have an axial length sufficient for the respective connection phases.

The female connector piece 4 comprises at its end opposite the introduction portion 12 a second connection 32 for a second flexible tube 34 which leads to a peritoneal catheter not illustrated in the drawings. The securing of the second tube 34 to the second connection 32 is for example by a clamp connection between the second connection 32 and the sleeve 10, by shrinking the tube 34 onto the second connection 32, by adhering, or the like.

The male connector piece 6 comprises a third connection 36 originating from the sleeve 21 for a third flexible tube 38 which establishes a connection between the male connector piece 6 and an empty bag for used dialysis solution. This third connection 36 is advantageously disposed in the vicinity of the first connection 18.

The receiving region 14 of the male connector piece is open by an opening 40 in the direction towards the female connector piece 4 to be introduced. Furthermore, the sleeve 21 of the male connector piece 6 comprises two regions of different internal diameters, a first sleeve region having an internal diameter which is greater than the external diameter of the introduction portion 12 of the sleeve 10 of the female connector piece, and a second sleeve region 44 which adjoins the first sleeve region 42 and has an internal diameter which is at least approximately equal to, preferably somewhat greater than, the external diameter of the introduction portion 12 of the female connector piece 4.

In the region of the opening 40 of the male connector piece 6 at least one and in the embodiment illustrated two pins 46 project radially inwardly from the second sleeve region 42. The radial extent of the pins 46 inwardly and their external diameter are dimensioned so that a form-locking engagement is possible with a guide groove 48 which is provided in a guide portion of the first sleeve 10 as will be explained in detail hereinafter with reference to FIGS. 3 to 7.

In the interior of the female connector piece 4 a valve means 52 is disposed. This valve means 52 comprises essentially an annular seal 54 made of suitable elastomeric material and held in an annular recess 56 in the inner wall of the introduction portion 12 of the first sleeve 10. The retaining of the seal 54 in the recess 56 is by adhering, force fit, a spring ring or the like.

The diameter of the opening 57 of the seal 54 is at least approximately equal to, preferably somewhat less than, an external diameter D of the main portion 28 of the tube section 22 in the male connector piece 6. On the other hand, the diameter of the opening 57 is greater than the external diameter E of the front portion 30 of the tube section 22.

Furthermore, the valve means 52 in the connector piece 4 comprises a valve plate 58 which by a suitable spring means, for example by a spiral pressure spring 60, is held in liquid-tight engagement with the annular sealing washer 54. The valve plate 58 is disposed between the seal 54 and the second connection 32 in the female connector piece 4.

The pressure spring 60 bears with its one end on a suitable spring seat 62 and a suitable configuration of the contour of the valve plate 58 facing the spring permits a form-locking engagement between the valve plate 58 and the pressure spring 60. In the region between the valve plate 58 and the spring seat 62 on the inner contour of the female connector piece 4 a stop 64 is provided in the form of a projecting region.

In the outer end region of the introduction portion 12 of the female connector piece 4, preferably adjacent the introduction opening 65, an annular sealing element is disposed, for example an O ring 66 which is advantageously let into an annular groove which is disposed on the outer surface of the female connector piece 4.

Hereinafter the mode of operation of the present connector will be described, in particular with reference to FIGS. 1 and 3 to 7:

In the state according to FIG. 1, i.e. in the unconnected state, both the female connector piece 4 and the male connector piece 6 are sealed with a cap, not illustrated in the drawings, the inner spaces sealed by the cap possibly being sterilized with a suitable disinfectant. To establish a first connection state in accordance with FIG. 3 firstly the two caps are removed and the female connector piece 4 is aligned with the male connector piece 6 in such a manner that the pin or pins 46 on the male connector piece 6 are in alignment with an entry portion 68 of the guide groove 48 on the guide portion 50 of the female connector piece 4.

Figure 7:
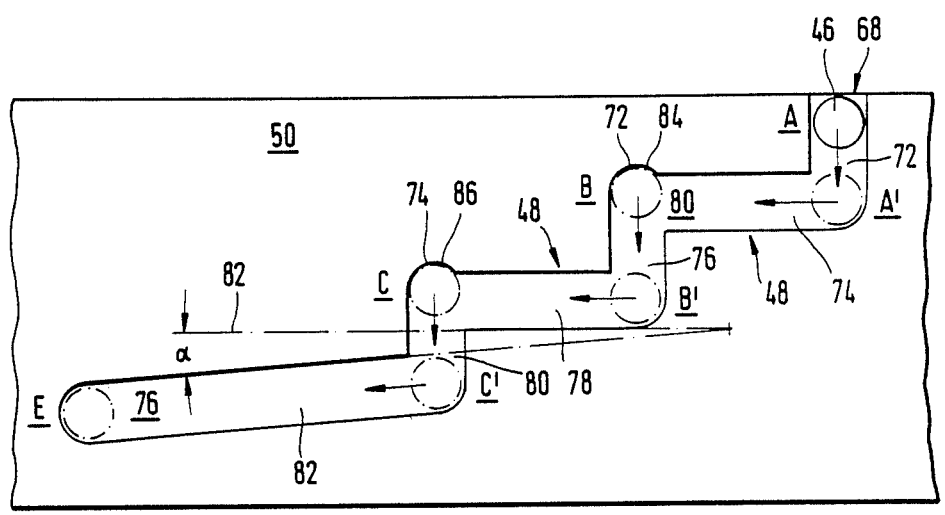
FIG. 7 shows a guide groove on the female connector piece in a developed representation.

The position of the pin 46 with respect to the guide groove 48 or to the entry 68 is designated in FIG. 7 by A. FIG. 7 shows the guide groove 48 in the developed illustration and it is seen that this is a three-stage bayonet path. If now the female connector piece 4 is pushed into the male connector piece 6 the pin 46 in the guide groove 48 first reaches a first coupling position which is marked in FIG. 7 by A'. In this coupling position the female connector piece 4 in the male connector piece 6 reaches a coupling position as shown in FIG. 3 in which the O ring engages sealingly on the inner peripheral surface of the second sleeve region 44 of the male connector piece 6. By relative rotation of the female connector piece 4 with respect to the male connector piece 6 the pin 46 follows the guide groove 48 and reaches a first locking position which is marked in FIG. 7 by B and in which the first coupling position is secured. In this first coupling position, which is shown in FIG. 3 and referred to hereinafter as flushing position, the valve plate 58 of the valve means 52 due to the pressure load by the spring 60 remains in liquid-tight engagement with the sealing washer 54 so that only a fluid passage from the first connection 18 through the central tube section 22 to the third connection 36 is possible. In this flushing position the full bag with the fresh dialysis solution is now opened, for example by breaking a breakage cone, and fresh dialysis solution flows through the first tube 20, the central tube section 22 and the third tube 38 into the empty bag. The entering fresh dialysis solution removes both the disinfectant which is disposed in these regions of the male and female connector pieces and particles which can form on opening the breakage cone, and flushes them into the empty bag.

After the flushing of the connector as second step in the peritoneal dialysis the used dialysis solution is drained from the peritoneal cavity of the patient into the empty bag.

For this purpose the female connector piece 4 is further introduced into the male connector piece 6, the pin 46 in the guide groove 48 reaching a second position designated in FIG. 7 by B'. A turning of the female connector piece 4 relatively to the male connector piece 6 brings the pin 46 into a position which is designated in FIG. 7 by C and which corresponds to the coupling position of FIG. 4, in which the second coupling position is secured.

An insertion of the female connector piece 4 into the male connector piece 6 first effects that the mouth opening 24 of the tube section 22 comes into engagement with a surface 70 of the valve plate 58 so that the supply of fresh dialysis solution from the full bag through the first flexible tube 20 is interrupted. A further movement of the female connector piece 4 into the male connector piece 6 (the pin 46 moving into the position B' of FIG. 7) leads finally to the second coupling position of FIG. 4. Once this second coupling position is reached the female connector piece is turned so that the pin 46 assumes in the guide groove 48 the position C in FIG. 7 in which said second coupling position is locked.

As apparent from FIG. 4, in said second coupling position the valve plate 58 is moved against the spring force of the pressure spring 60 by the central tube section 22 out of engagement with the sealing washer 54 so that a fluid passage becomes free from the second connection 32 of the female connector piece past the valve plate 58 and through the annular free space 71 formed between the opening 57 of the annular sealing washer 54 and the outer surface of the front portion 30 of the central tube section 22 to the third connection 36. The used dialysis liquid flows through this fluid passage from the peritoneal cavity of the patient into the empty bag as indicated in FIG. 4 by the flow arrows.

The surface 70 of the valve plate 58 is pressed by the pressure spring 60 against the mouth opening 24 of the tube section 22 so that no fresh dialysis solution can flow from the full bag. This second coupling position is also referred to as drain or discharge position.

After the used dialysis solution has flown from the peritoneal cavity of the patient completely into the empty bag the third step of supplying fresh dialysis solution from the full bag to the peritoneal cavity takes place. For this purpose, firstly the female connector piece is brought out of the second connection state of FIG. 4 into a third coupling position according to FIG. 5, the pin 46 moving in accordance with FIG. 7 out of the position C into the position C'. In this third coupling position, also referred to as intermediate position, the mouth opening 24 of the inner tube 22 remains sealed by the surface 70 of the valve plate 58 so that no fresh dialysate can flow from the first tube 20. Furthermore, the main portion 28 of the tube section 22 seals in this third connection state the opening 57 of the annular sealing washer 54 and thus the annular free space 71 so that no fluid passages exist between the first, second and third connections. Of great importance here is that the material from which the seal 54 is made is an elastomer so that a reliable liquid-tight engagement exists between the main portion 28 of the tube section 22 and the annular sealing washer 54.

To permit fresh dialysis solution from the full bag to enter the peritoneal cavity, the female connector piece 4 is turned relatively to the male connector piece 6 so that the pin 46 moves out of the position C' in FIG. 7 to a position E in FIG. 7. As apparent from FIG. 7 the path of the guide groove 48 from the position C' up to the position E is no longer parallel to the two paths from A' to B and B' to C respectively but is inclined downwardly thereto at an angle α, α advantageously being 5 degrees. If therefore the female connector piece 4 is turned out of the third coupling position of FIG. 5 the pin 46 in the guide groove 48 is subjected to a thread guiding and as a result the female connector piece 4 is screwed linearly and uniformly into the male connector piece 6 until the pin 46 has reached the position E in FIG. 7. Once the pin 46 has reached the position E in FIG. 7 a fourth coupling position or entry position according to FIG. 6 is reached.

In the uniform advance movement of the female connector piece 4 into the male connector piece 6 the valve plate 58 is first moved against the force of the pressure spring 60, on the one hand the mouth opening 24 of the tube section 22 remaining sealed by the surface 70 of the valve plate 58 and on the other hand the outer surface of the main portion 28 of the tube section 22 remaining in liquid-tight engagement with the opening 57 of the sealing washer 54. In the course of the further movement of the female connector piece 4 into the male connector piece 6 the valve plate 58 comes into one-sided engagement with the stop 64 in the female connector piece 4 so that on further movement of the female connector piece 4 into the male connector piece 6 said valve plate is tilted out of its horizontal position according to FIGS. 1, 3, 4 and 5 with simultaneous deformation of the pressure spring 60 as illustrated in FIG. 6. By this tilting of the valve plate 58 the mouth opening 24 of the tube section 22 is continuously released so that a fluid passage is freed from the first connection 18 through the tube section 22, the mouth opening 24 and through the coil of the spring 60 up to the second connection 32. Through this fluid passage fresh dialysis solution can now flow from the full bag into the peritoneal cavity of the patient as illustrated in FIG. 6 by the flow arrows.

On appropriate formation of both the surface of the valve plate 58 and the inclination angle of the last course of the guide groove 48 a linearly uniform opening of the mouth opening 24 can be achieved so that the dialysis solution flows from the full bag with continuously increasing flow rate and continuously increasing flow volume into the peritoneal cavity.

When the dialysis solution has flowed completely out of the full bag into the peritoneal cavity of the patient the previously described steps are then carried out in the reverse order, i.e. firstly the female connector piece 4 is turned relatively to the male connector piece 6 to reach the third coupling position of FIG. 5 in which the access to the peritoneal cavity is again closed by the valve plate 58 which seals the mouth opening 24 of the tube section 22. By appropriate turning and pulling movements the female connector piece 4 is then disconnected from the male connector piece 4 is then disconnected from the male connector piece 6, passing consecutively through the coupling positions according to FIGS. 4 and 3 until the disconnected state according to FIG. 1 is again reached.

The open end of the female connector piece 4 is now again sprayed with a suitable disinfectant and sealed with a cap and the male connector piece 6, the full bag and the empty bag in which the used dialysis solution is disposed are disposed of as a unit.

Below, with reference to FIG. 7 the exact structure of the guide groove 48 in the guide portion 50 will be explained:

As already mentioned, the guide groove 48 represents a three-stage bayonet track or path so that the pin 46 during its movement in the guide groove 48 causes the female connector piece 4 to execute lifting and rotary movements with respect to the male connector piece 6. For this purpose the guide groove 48 consists of the following portions:

A first lifting portion 72 is followed by a first rotary portion 74 from which a second lifting portion 76 extends which in turn merges into a second rotary portion 78 which continues into a third lifting portion 80. From said third lifting portion 80 a screw portion 82 extends which permits a combined rotary/lifting movement.

Whereas the lifting portions 72, 76 and 80 are aligned substantially parallel to the connection axis, the rotary portions 74 and 78 extend substantially perpendicularly to the connection axis. On the other hand, the screw portion 82 is inclined with respect to the connection axis by the aforementioned angle α.

To secure the position of the pin 46 at the point B, the first turning or rotary portion 74 is provided at its intersection with the second lifting portion 64 advantageously with a detent or notch 84 in which the pin 46 can assume a secured rest position so that the first coupling position according to FIG. 3 is secured.

In similar manner the second coupling position according to position C of FIG. 4 is to be secured in that the second rotary portion 78 comprises at its intersection with the third lifting portion 80 also a formed notch 86 which secures the pin 46 in the second coupling position. Since in this position according to FIG. 4 the pressure spring 60 is already compressed a certain amount, the pin 46 is pressed into the second notch 76 and secured there by the spring force which tends to separate the female connector piece 4 from the male connector piece 6.

As already mentioned, the screw portion 82 of the bayonet path is inclined an angle α to the connection axis of the connector 2. Due to the spring force of the pressure spring 60 the pin 46 is pressed in its final end position at E against the bayonet path and there held without further detent or notch only by frictional engagement.

Summarizing, with the connector described above a rapid and thorough flushing of the connector prior to the dialysis operation is possible using a minimum of dialysis solution and furthermore the use of roller clamps in the corresponding supply lines can be completely dispensed with because the opening and closing of the corresponding fluid passages is effected solely by the movement of the connector itself. Thus, increased reliability and safety, in particular in CAPD, is always ensured.

The selection of the materials for making the connector according to the invention is within the scope of the expert, physiologically neutral metals and/or plastics being used.

I claim:

1. A continual ambulant peritoneal dialysis tube connection device comprising:
   a male connector piece having a central tube section joined to and surrounded by a protective sleeve, a receiving region between said central tube and protective sleeve, a first connection means for connecting a first dialysis solution bag, and a third connection means for connecting a second dialysis solution bag;
   a female connector piece having a valve means, an introduction portion, a second connection means for connecting a peritoneal catheter, and an annular seal;
   said valve means having a valve plate for providing a fluid barrier in its uncoupled state prohibiting the flow of fluids through its elongated axial direction;
   said introduction portion forming a liquid-tight seal between said protective sleeve on said male connector piece and said female connector piece after being inserted into said receiving region.;
   said first connection means being in fluid communication with said central tube section;
   said valve means cooperating with said central tube section and the inserted position of said female connector within said protective sleeve providing for selective fluid communication between any two of said first connection means, said second connection means, and said third connection means;
   said central tube section having a mouth opening forming a fluid-tight seal with said valve plate when said mouth opening contacts said valve plate, whereby said male connector piece (6) in a first coupling position with said female connector piece (4) in fluid-tight manner with said annular seal (66) effects a first fluid passage from said first connection means (18) to said third connection means (36), when in a second coupling position by said central tube section (22) of said male connector piece (6) interacting with said valve means (52) within said female connector piece (4) opens said valve, said mouth opening (24) of said central section (22) having a fluid-tight sealing manner on said valve plate (58) and said front portion (30) passing through an opening (57) of said annular seal (56) to effect a second fluid passage from said second connection means (32) to said third connection means (36), and when in a third coupling position said main portion (28) of said central tube section (22) of said male connector piece (6) forming a fluid-tight seal with said annular seal (56) of said female connector piece (4) and said valve plate (58) being tilted from said mouth opening (24) of said central tube section (22) forming a third fluid passage from said first connection means (18) to said second connection means (32), each of the coupling positions are predetermined and lockable by a connecting means.

2. The connection device of claim 1 further comprising:
   a connecting means for securely positioning said female connector piece within said male connector piece.

3. The connection device of claim 2 wherein said connecting means further comprises:
   at least one pin (46) on said male connector piece (6); and
   said female connector piece having a guide groove (48) receiving said pin.

4. The connection device of claim 3 further comprising:
   said guide groove (48) extending in stepped manner along the peripheral direction of a sleeve (10) on said female connector piece (4).

5. The connection device of claim 4 wherein said guide groove (48) further comprises:
   a first lifting portion (72);
   a second lifting portion (76);
   a first rotary portion (74) and a second rotary portion (78);
   said first rotary portion connecting to said first lifting portion and second lifting portion;
   a third lifting portion (80);
   said second rotary portion connecting to said second lifting portion (76) and said third lifting portion (80); and
   a screw portion (82) extending from said third lifting portion (80).

6. The connection device of claim 5 wherein said guide groove further comprises:
   said screw portion (82) inclined to a center axis of said connection device (2).

7. The connection device of claim 1 wherein said valve means (52) further comprises:
   a biasing means resulting in fluid-tight connection between said valve plate and said annular seal.

8. The connection device of claim 7 wherein said valve plate (58) and said annular seal (54) further comprise an elastomeric material.

9. The connection device of claim 7 further comprising:
   said valve plate (58) being biased by a pressure spring (60) towards said annular seal (54).

10. The connection device of claim 9 further comprising:
    a stop (64) causing said valve plate (58) to tilt when said central tube section causes said valve plate to contact said stop.

11. The connection device of claim 1 wherein said female connector piece (4) further comprises:
    an annular sealing member adjacent said introduction portion (12).

12. The connection device of claim 11 wherein said sealing member further comprises an O ring (66).

13. The connection device of claim 1 wherein said central tube section (22) further comprises:
    a front portion (30) having a first external diameter;
    a main portion having a second external diameter greater than said first external diameter;
    said annular seal positioned within said female connector having an internal diameter;
    said second external diameter being at least equal to said internal diameter; and
    said first external diameter being less than said internal diameter.

* * * * *